United States Patent [19]
Curry et al.

[11] Patent Number: 6,156,803
[45] Date of Patent: Dec. 5, 2000

[54] AQUEOUS, FLOWABLE SUSPENSION CONCENTRATE OF AN AGRICULTURALLY ACTIVE CHEMICAL, AND SPRAYABLE USE FORMULATION THEREOF

[75] Inventors: James F. Curry; Ronald H. Goehner, Jr.; Kolazi S. Narayanan, all of Wayne, N.J.; Domingo Jon, New York, N.Y.

[73] Assignee: ISP Investments Inc, Wilmington, Del.

[21] Appl. No.: 09/164,541

[22] Filed: Sep. 30, 1998

Related U.S. Application Data

[60] Provisional application No. 60/061,824, Oct. 14, 1997.

[51] Int. Cl.⁷ ..................................................... A01N 25/04
[52] U.S. Cl. ..................................... 514/772.2; 514/772.1; 514/772; 514/937; 514/938; 504/363
[58] Field of Search ..................................... 514/772, 951, 514/952, 970; 504/116; 562/595

[56] References Cited

U.S. PATENT DOCUMENTS

| | | | |
|---|---|---|---|
| 3,956,480 | 5/1976 | Dichter et al. | 424/54 |
| 4,867,972 | 9/1989 | Girardeau et al. | 424/81 |
| 5,653,965 | 8/1997 | Narayanan et al. | 424/59 |

FOREIGN PATENT DOCUMENTS

96/16539  6/1996  WIPO.

*Primary Examiner*—S. Mark Clardy
*Assistant Examiner*—Pernell W. Williams
*Attorney, Agent, or Firm*—Walter Katz; William J. Davis; Marilyn J. Maue

[57] ABSTRACT

What is described is an aqueous, flowable suspension concentrate of an agriculturally active chemical having excellent dilution and storage stability, and sprayable aqueous use formulation thereof, containing partially neutralized alkyl vinyl ether-maleic acid half-ester copolymers as dispersing agents therein.

10 Claims, No Drawings

AQUEOUS, FLOWABLE SUSPENSION CONCENTRATE OF AN AGRICULTURALLY ACTIVE CHEMICAL, AND SPRAYABLE USE FORMULATION THEREOF

CROSS-REFERENCE TO RELATED PATENT APPLICATION

This application is based on Provisional Application Ser. No. 60/061,824, filed Oct. 14, 1997.

BACKGROUND OF THE INVENTION

1. Field of the Invention

This invention relates to an aqueous, flowable suspension concentrate of an agriculturally active chemical, and to sprayable use formulations thereof, and, more particularly, to suspension concentrates and use formulations containing partially neutralized alkyl vinyl ether-maleic acid half-ester copolymers as dispersing agents therein.

2. Description of the Prior Art

A water-based suspension concentrate, or aqueous flowable, and sprayable dilution compositions thereof, are formulation types which allow water-insoluble agriculturally active chemicals to be delivered easily, with no risk of dust or flammability. However, it is necessary that such suspension concentrates and use formulations thereof, should permit the active to remain stable and essentially insoluble in water both in the concentrate and in the use formulation.

Accordingly, it is an object of this invention to provide suspension concentrates which have excellent suspensibility properties after dilution and excellent storage stability properties. Another object of the invention is to provide suspension concentrates which possess a suspensibility after-dilution of at least 60% after a 4 hour period of settling; and substantially no settling after storage for 2 weeks at 52° C.

Still another object herein is to provide suspension concentration which, upon a 25–1000X dilution with water, provides a sprayable, suspension formulation at a 1% active level.

SUMMARY OF THE INVENTION

What is provided herein is an, aqueous, flowable suspension concentrate of an agriculturally active chemical, and diluted, aqueous sprayable use formulations thereof, for spraying onto crops and animals, which contain partially neutralized alkyl vinyl ether-maleic acid half-ester copolymers as dispersing agents therein.

DETAILED DESCRIPTION OF THE INVENTION

The suspension concentrates of the invention containing an agriculturally active ingredient were prepared using the following actives:
chlorothalonil (tetrachloroisophthalonitrile) fungicide; a thiophene-substituted carboxamide fungicide; carbaryl (1-napthyl methylcarbamate) insecticide; and atrazine (6-chloro-N-ethyl-N-isopropyl-1,3,5-triazine-2,4-diamine) herbicide. Typical suspension concentrates of chlorothalonil, carbaryl and atrazine were prepared to give active concentrations of 41%, 41%, and 43% w/w, respectively, which represent 4 pounds of active ingredient per gallon of water.

The suspension concentrates were wet-milled using an Eiger Machinery Model #100 before testing. Prior to feeding into the wet mill, compositions were mixed using a homogenizer. Typically, a 70% to 80% loading of 0.1 cm zirconium oxide beads was used and concentrates of 150 g were milled for 10 minutes at 3000 rpm. The temperature of the cooling bath was typically −5° C. to 0° C., which gave a milling temperature between 15° C. and 21° C. for the concentrates. The operating conditions of the wet-mill resulted in about 1⅓ passes of the concentrate per minute.

Suspensibility tests on the suspension concentrates were performed in 1000 (17.5 g $CaCl_2$, 8.14 g $MgCl_2.6H_2O$ in 20 l water) and 5000 ppm hard water according to CIPAC Test #MT 161. Tests were run in duplicate and reported with a standard deviation. The test was run using a calculated weight of the suspension concentrate to give 1% active by weight when diluted into 250 ml of hard water. After 4 hours, 90% of the dispersion was decanted off and discarded, and the remaining 10% of the dispersion was centrifuged at 2000 rpm for 15 minutes, followed by drying and weighing of the solid active retrieved. The results are reported as percent suspended active by weight. Diluted suspensions were also evaluated by measuring bloom and sediment in Nessler tubes. A 1 ml aliquot of concentrate was introduced into 49 ml of hard water contained in a Nessler tube. Initial bloom was observed at zero time and the quality of the bloom was graded by visual appearance. The tube was inverted 20 times and the stability evaluated by measuring the height of the sediment (ppt or cream) at intervals of 1, 2, 4, and 24 hours. A redispersion test was carried out after 24 hours by counting the number of inversions necessary to remove the settled solids from the bottom of the Nessler tube.

Storage stability tests also were carried out by storing the suspensions at 52° C. in clear, wide-mouth glass bottles. 50 ml of each suspension was introduced into a bottle (5 cm×5 cm, diameter×height), capped, and placed in the oven. After two weeks, the suspensions were allowed to cool. The height of any separation at the top was measured, and any sedimentation was detected by probing the bottom of the suspensions with thin, wooden applicators. The suspensions were shaken on a horizontal platform shaker for 15 minutes. Aliquots were then removed for suspensibility testing.

Suitable aqueous, flowable suspension concentrates in accordance with the invention are diluted in hard water to give 1% active. A sprayable use suspension formulation is obtained upon dilution. After 4 hours, the diluted suspension has a suspensibility of at least 60%. These systems, in which the copolymer functions as a dispersing agent, have the following compositions:

TABLE 1

| | % by Weight | |
|---|---|---|
| | Suitable | Preferred |
| Essential Ingredients | | |
| Agriculturally Active Chemical | 20–80 | 30–70 |
| Partially Neutralized Alkyl Vinyl Ether-Maleic Acid Half-Ester | 0.1–5 | 0.2–1.5 |
| Thickener | 0.05–0.5 | 0.1–0.2 |
| Water | 20–80 | 30–70 |
| pH | 2–9 | 3–7 |
| Optional Ingredients | | |
| wetting agent, preservative, antifreeze, antifoam, other agricultural adjuvants | | |

The compositions of the present invention are useful for obtaining suspension concentrates which give excellent suspensibility properties after dilution and excellent storage stability properties using MVE copolymers as dispersing agents.

EXAMPLE 1

Methyl vinyl ether-maleic acid isopropyl half-ester copolymer (MVEIM), is available commercially as a 50% polymer resin in isopropanol. The repeat unit structure of the copolymer is shown below, where $R_1$ is -iso-$C_3H_7$.

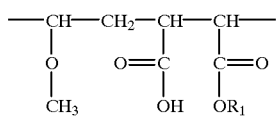

FIGURE 1

The molecular weight of the repeat unit is 216 g/mole and therefore 1 gram of polymer contains $4.63 \times 10^{-3}$ mole of free acid. In order to achieve 40 mole % neutralization of the copolymer, 0.4 moles of base must be combined to each mole of repeat unit. Therefore, for 1 gram of polymer, $1.85 \times 10^{-3}$ mole of base is needed (0.4 mole/216 g/mole). A procedure to obtain a 40% neutralized copolymer using sodium hydroxide is described below. 750 grams of MVEIM resin (375 g polymer) are charged into a 2 liter jacketed distillation reactor equipped with an agitator. 321 ml of water is added to the resin to reduce the concentration from 50% to 35%. 55.5 g of 50% NaOH w/w is added to the mixture, the amount needed to give 40% neutralization. The temperature of the reactor is raised to approximately 82° C. to distill off the isopropanol. As isopropanol is distilled from the reactor, it is replaced with water. As the isopropanol is removed, 795 g of water is added. The resulting polymer, to be referred to as Copolymer 1A, is a 40% neutralized sodium salt of MVEIM. A 1500 g aqueous solution of 25% equivalent MVEIM copolymer is obtained. In order to prepare a copolymer that is 50% neutralized, the same procedure as outlined for Copolymer 1A is used, except 69.4 g of 50% NaOH is used. The finished product, to be referred to as Copolymer 1B, is a 50% neutralized sodium salt of MVEIM. A 1500 g aqueous solution of 25% equivalent MVEIM copolymer is obtained. In order to prepare a copolymer that is 30% neutralized, the same procedure as outlined for Copolymer 1A is used, except 41.6 g of 50% NaOH is used. The finished product, to be referred to as Copolymer 1C, is a 30% neutralized sodium salt of MVEIM. A 1500 g aqueous solution of 25% equivalent MVEIM copolymer is obtained.

EXAMPLE 2

A procedure to obtain a 40% neutralized copolymer of MVEIM using ammonium hydroxide is identical to the one described in Example 1, except that 242.9 g of a 10% w/w $NH_4OH$ solution is added instead of NaOH solution. The finished product, to be referred to as Copolymer 2, is a 40% neutralized ammonium salt of MVEIM. A 1500 g aqueous solution of 25% equivalent MVEIM copolymer is obtained.

EXAMPLE 3

A procedure to obtain a 40% neutralized copolymer of MVEIM using 2-amino-2-methyl-1-propanol is identical to the one described in Example 1, except that 65.0 g of a 95% w/w 2-amino-2-methyl-1-propanol solution (AMP solution) is added instead of NaOH solution. The finished product, to be referred to as Copolymer 3, is a 40% neutralized AMP salt of MVEIM. A 1500 g aqueous solution of 25% equivalent MVEIM copolymer is obtained.

EXAMPLE 4

A procedure to obtain a 40% neutralized copolymer of MVEIM using potassium hydroxide is identical to the one described in Example 1, except that 86.4 g of a 45% w/w potassium hydroxide solution is added instead of NaOH solution. The finished product, to be referred to as Copolymer 4, is a 40% neutralized potassium salt of MVEIM. A 1500 g aqueous solution of 25% equivalent MVEIM copolymer is obtained.

EXAMPLE 5

Copolymer 1A from Example 1 can be spray dried to give a copolymer product in powder form. Water is added to Copolymer 1A to reduce the concentration from 25% to 15% polymer, thereby reducing viscosity. The 15% polymer solution is fed into a Yamato Model GA32 Pulvis Mini Spray Dryer, with inlet temperature maintained at 200° C. A white, free flowing powder of Copolymer 1A is obtained.

EXAMPLE 6

Copolymer 2 from Example 2 can be spray dried to give a copolymer product in powder form. Water is added to Copolymer 2 to reduce the concentration from 25% to 15% polymer, thereby reducing viscosity. The 15% polymer solution is fed into a Yamato Model GA32 Pulvis Mini Spray Dryer, with inlet temperature maintained at 200° C. A white, free flowing powder of Copolymer 2 is obtained

EXAMPLE 7

Copolymer 3 from Example 3 can be spray dried to give a copolymer product in powder form. Water is added to Copolymer 3 to reduce the concentration from 25% to 15% polymer, thereby reducing viscosity. The 15% polymer solution is fed into a Yamato Model GA32 Pulvis Mini Spray Dryer, with inlet temperature maintained at 200° C. A white, free flowing powder of Copolymer 3 is obtained

EXAMPLE 8

Copolymer 4 from Example 4 can be spray dried to give a copolymer product in powder form. Water is added to Copolymer 4 to reduce the concentration from 25% to 15% polymer, thereby reducing viscosity. The 15% polymer solution is fed into a Yamato Model GA32 Pulvis Mini Spray Dryer, with inlet temperature maintained at 200° C. A white, free flowing powder of Copolymer 4 is obtained

EXAMPLE 9

Methyl vinyl ether-maleic acid butyl ester copolymer (MVEBM), is available commercially as a 50% polymer resin in ethanol. The repeat unit structure of the copolymer is shown in FIG. 1, where $R_1$ is —$C_4H_9$. A procedure to obtain a 40% neutralized copolymer of MVEBM using sodium hydroxide is identical to the one described in Example 1, except that 52.1 g of a 50% w/w sodium hydroxide solution is added instead of 55.5 g. The finished product, to be referred to as Copolymer 9, is a 40% neutralized sodium salt of MVEBM. A 1500 g aqueous solution of 25% equivalent MVEBM copolymer is obtained.

EXAMPLE 10

A procedure to obtain a 40% neutralized copolymer of MVEBM using potassium hydroxide is identical to the one described in Example 9, except that 81.2 g of a 45% w/w potassium hydroxide solution is added instead of NaOH solution. The finished product, to be referred to as Copolymer 10, is a 40% neutralized potassium salt of MVEBM. A 1500 g aqueous solution of 25% equivalent MVEIM copolymer is obtained.

EXAMPLE 11

Methyl vinyl ether-maleic acid ethyl ester copolymer (MVEEM), is available commercially as a 50% polymer resin in ethanol. The repeat unit structure of the copolymer is shown in FIG. 1, where $R_1$ is $-C_2H_5$. A procedure to obtain a 40% neutralized copolymer of MVEEM using sodium hydroxide is identical to the one described in Example 1, except that 59.3 g of a 50% w/w sodium hydroxide solution is added instead of 55.5 g. The finished product, to be referred to as Copolymer 11, is a 40% neutralized sodium salt of MVEEM. A 1500 g aqueous solution of 25% equivalent MVEEM copolymer is obtained.

EXAMPLE 12

A procedure to obtain a 40% neutralized copolymer of MVEEM using potassium hydroxide is identical to the one described in Example 11, except that 92.4 g of a 45% w/w potassium hydroxide solution is added instead of NaOH solution. The finished product, to be referred to as Copolymer 12, is a 40% neutralized potassium salt of MVEEM. A 1500 g aqueous solution of 25% equivalent MVEEM copolymer is obtained.

EXAMPLE 13

Neutralized Copolymer 9 can be partially hydrolyzed by placing the solution in a capped bottle in an oven at 70° C. for two weeks. Approximately 50% of the ester is hydrolyzed to the corresponding acid. The hydrolyzed portion of the structure is shown in FIG. 1 where $R_1$ is $-H$. The neutralized, partially hydrolyzed copolymer will be referred to as Copolymer 13.

EXAMPLE 14

Neutralized Copolymer 11 can be partially hydrolyzed by placing the solution in a capped bottle in an oven at 70° C. for two weeks. Approximately 50% of the ester is hydrolyzed to the corresponding acid. The hydrolyzed portion of the structure is shown in FIG. 1 where $R_1$ is $-H$. The neutralized, partially hydrolyzed copolymer will be referred to as Copolymer 14.

EXAMPLE 15

In order to prepare 150 g of a 41% carbaryl aqueous suspension concentrate, an aqueous stock solution of thickener, preservative, antifreeze, and antifoam, to be referred to as Stock Solution A, is prepared according to the following composition by weight:

Stock Solution A

| Ingredient | Composition, % |
| --- | --- |
| Xanthan | 0.15 |
| Propylene glycol | 11.10 |
| Proxel GXL | 1.16 |
| Rhodorsil 426R | 1.16 |
| Water | 86.43 |

56.9 g of Stock Solution A is mixed with 31.6 g of an aqueous solution containing 2.37% of Copolymer 1A. To this mixture 61.5 g of carbaryl is added, giving a 150 g dispersion, which is homogenized using an IKA Ultra-Turrax Homogenizer. The dispersion is transferred to an Eiger Mill Model #100, equipped with 1 mm zirconium beads and a water-cooled jacket operated at −5° C. The dispersion is milled for 10 minutes at 3000 rpm. The resulting suspension concentrate, to be referred to as Formulation 1, has a composition by weight shown below:

Formulation 1

| Ingredient | Composition, % |
| --- | --- |
| Carbaryl | 41.0 |
| Copolymer 1A | 0.5 |
| Propylene glycol | 4.2 |
| Proxel GXL | 0.44 |
| Rhodorsil 426R | 0.44 |
| Xanthan | 0.06 |
| Water | 53.36 |

Formulation 1 was tested for suspensibility after dilution for 4 hours according to CIPAC MT161 by weighing 6.1 g into a 250 ml stoppered graduated cylinder which was then filled to the mark with 1000 ppm hard water. The cylinder was inverted 30 times and left to stand for 4 hours. The residual solids in the bottom 10% of the suspension was collected as described above. For Formulation 1, percent suspended carbaryl after 4 hours was 93.2±0.2%.

EXAMPLE 16

In order to prepare 150 g of a 41% carbaryl suspension concentrate, 56.9 g of Stock Solution A (from Example 15) is mixed with 31.6 g of an aqueous solution containing 2.37% of Copolymer 2. To this mixture 61.5 g of carbaryl is added, giving a 150 g dispersion, which is homogenized and milled as described in Example 15. The resulting suspension concentrate, to be referred to as Formulation 2, has a composition by weight shown below:

Formulation 2

| Ingredient | Composition, % |
| --- | --- |
| Carbaryl | 41.0 |
| Copolymer 2 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 2 was tested for suspensibility as described in Example 15 and percent suspended carbaryl after 4 hours was 91.9±0.3%.

EXAMPLE 17

In order to prepare 150 g of a 41% carbaryl suspension concentrate, 56.9 g of Stock Solution A (from Example 15) is mixed with 31.6 g of an aqueous solution containing 2.37% of Copolymer 3. To this mixture 61.5 g of carbaryl is added, giving a 150 g dispersion, which is homogenized and milled as described in Example 15. The resulting suspension concentrate, to be referred to as Formulation 3, has a composition by weight shown below:

Formulation 3

| Ingredient | Composition, % |
| --- | --- |
| Carbaryl | 41.0 |
| Copolymer 3 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 3 was tested for suspensibility as described in Example 15 and percent suspended carbaryl after 4 hours was 93.3±0.4%.

EXAMPLE 18

In order to prepare 150 g of a 41% carbaryl suspension concentrate, 56.9 g of Stock Solution A (from Example 15) is mixed with 31.6 g of an aqueous solution containing 2.37% of Copolymer 4. To this mixture 61.5 g of carbaryl is added, giving a 150 g dispersion, which is homogenized and milled as described in Example 15. The resulting suspension concentrate, to be referred to as Formulation 4, has a composition by weight shown below:

Formulation 4

| Ingredient | Composition, % |
| --- | --- |
| Carbaryl | 41.0 |
| Copolymer 4 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 4 was tested for suspensibility as described in Example 15 and percent suspended carbaryl after 4 hours was 92.1±0.6%.

EXAMPLE 19

In order to prepare 150 g of a 41% carbaryl suspension concentrate, 56.9 g of Stock Solution A (from Example 15) is mixed with 31.6 g of an aqueous solution containing 2.37% of Copolymer 5. To this mixture 61.5 g of carbaryl is added, giving a 150 g dispersion, which is homogenized and milled as described in Example 15. The resulting suspension concentrate, to be referred to as Formulation 5, has a composition by weight shown below:

Formulation 5

| Ingredient | Composition, % |
| --- | --- |
| Carbaryl | 41.0 |
| Copolymer 5 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 5 was tested for suspensibility as described in Example 15 and percent suspended carbaryl after 4 hours was 90.4±0.5%.

EXAMPLE 20

In order to prepare 150 g of a 41% carbaryl suspension concnetrate, 56.9 g of Stock Solution A (from Example 15) is mixed with 31.6 g of an aqueous solution containing 2.37% of Copolymer 6. To this mixture 61.5 g of carbaryl is added, giving a 150 g dispersion, which is homogenized and milled as described in Example 15. The resulting suspension concentrate, to be referred to as Formulation 6, has a composition by weight shown below:

Formulation 6

| Ingredient | Composition, % |
| --- | --- |
| Carbaryl | 41.0 |
| Copolymer 6 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 6 was tested for suspensibility as described in Example 15 and percent suspended carbaryl after 4 hours was 94.1±0.2%.

EXAMPLE 21

In order to prepare 150 g of a 41% carbaryl suspension concnetrate, 56.9 g of Stock Solution A (from Example 15) is mixed with 31.6 g of an aqueous solution containing 2.37% of Copolymer 7. To this mixture 61.5 g of carbaryl is added, giving a 150 g dispersion, which is homogenized and milled as described in Example 15. The resulting suspension concentrate, to be referred to as Formulation 7, has a composition by weight shown below:

Formulation 7

| Ingredient | Composition, % |
| --- | --- |
| Carbaryl | 41.0 |
| Copolymer 7 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 7 was tested for suspensibility as described in Example 15 and percent suspended carbaryl after 4 hours was 92.6±0.4%.

EXAMPLE 22

In order to prepare 150 g of a 41% carbaryl suspension concnetrate, 56.9 g of Stock Solution A (from Example 15) is mixed with 31.6 g of an aqueous solution containing 2.37% of Copolymer 8. To this mixture 61.5 g of carbaryl is added, giving a 150 g dispersion, which is homogenized and milled as described in Example 15. The resulting suspension concentrate, to be referred to as Formulation 8, has a composition by weight shown below:

Formulation 8

| Ingredient | Composition, % |
| --- | --- |
| Carbaryl | 41.0 |
| Copolymer 8 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 8 was tested for suspensibility as described in Example 15 and percent suspended carbaryl after 4 hours was 91.1±0.6%.

EXAMPLE 23

In order to prepare 150 g of a 41% carbaryl suspension, 56.9 g of Stock Solution A is mixed with 31.6 g of an aqueous solution containing 2.37% of Copolymer 9. To this mixture 61.5 g of carbaryl is added, giving a 150 g dispersion, which is homogenized and milled as described in Example 15. The resulting suspension concentrate, to be referred to as Formulation 9, has a composition by weight shown below:

Formulation 9

| Ingredient | Composition, % |
| --- | --- |
| Carbaryl | 41.0 |
| Copolymer 9 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 9 was tested for suspensibility as described in Example 15 and percent suspended carbaryl after 4 hours was 95.4±0.2%.

EXAMPLE 24

In order to prepare 150 g of a 41% carbaryl suspension concentrate, 56.9 g of Stock Solution A (from Example 15) is mixed with 31.6 g of an aqueous solution containing 2.37% of Copolymer 10. To this mixture 61.5 g of carbaryl is added, giving a 150 g dispersion, which is homogenized and milled as described in Example 15. The resulting suspension concentrate, to be referred to as Formulation 10, has a composition by weight shown below:

Formulation 10

| Ingredient | Composition, % |
| --- | --- |
| Carbaryl | 41.0 |
| Copolymer 10 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 10 was tested for suspensibility as described in Example 15 and percent suspended carbaryl after 4 hours was 91.6±0.3%.

EXAMPLE 25

In order to prepare 150 g of a 41% carbaryl suspension concentrate, 56.9 g of Stock Solution A (from Example 15) is mixed with 31.6 g of an aqueous solution containing 2.37% of Copolymer 11. To this mixture 61.5 g of carbaryl is added, giving a 150 g dispersion, which is homogenized and milled as described in Example 15. The resulting suspension concentrate, to be referred to as Formulation 11, has a composition by weight shown below:

Formulation 11

| Ingredient | Composition, % |
| --- | --- |
| Carbaryl | 41.0 |
| Copolymer 11 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 11 was tested for suspensibility as described in Example 15 and percent suspended carbaryl after 4 hours was 93.5±0.7%.

EXAMPLE 26

In order to prepare 150 g of a 41% carbaryl suspension concentrate, 56.9 g of Stock Solution A (from Example 15) is mixed with 31.6 g of an aqueous solution containing 2.37% of Copolymer 12. To this mixture 61.5 g of carbaryl is added, giving a 150 g dispersion, which is homogenized and milled as described in Example 15. The resulting suspension concentrate, to be referred to as Formulation 12, has a composition by weight shown below:

Formulation 12

| Ingredient | Composition, % |
| --- | --- |
| Carbaryl | 41.0 |
| Copolymer 12 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 12 was tested for suspensibility as described in Example 15 and percent suspended carbaryl after 4 hours was 92.7±0.3%.

EXAMPLE 27

In order to prepare 150 g of a 41% carbaryl suspension concentrate, 56.9 g of Stock Solution A (from Example 15) is mixed with 31.6 g of an aqueous solution containing 2.37% of Copolymer 13. To this mixture 61.5 g of carbaryl is added, giving a 150 g dispersion, which is homogenized and milled as described in Example 15. The resulting suspension concentrate, to be referred to as Formulation 13, has a composition by weight shown below:

Formulation 13

| Ingredient | Composition, % |
|---|---|
| Carbaryl | 41.0 |
| Copolymer 13 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 13 was tested for suspensibility as described in Example 15 and percent suspended carbaryl after 4 hours was 90.8±0.4%.

EXAMPLE 28

In order to prepare 150 g of a 41% carbaryl suspension concentrate, 56.9 g of Stock Solution A (from Example 15) is mixed with 31.6 g of an aqueous solution containing 2.37% of Copolymer 14. To this mixture 61.5 g of carbaryl is added, giving a 150 g dispersion, which is homogenized and milled as described in Example 15. The resulting suspension concentrate, to be referred to as Formulation 14, has a composition by weight shown below:

Formulation 14

| Ingredient | Composition, % |
|---|---|
| Carbaryl | 41.0 |
| Copolymer 14 | 0.5 |
| Propylene glycol | 4.2 |
| Proxel GXL | 0.44 |
| Rhodorsil 426R | 0.44 |
| Xanthan | 0.06 |
| Water | 53.36 |

Formulation 14 was tested for suspensibility as described in Example 15 and percent suspended carbaryl after 4 hours was 92.6±0.6%.

EXAMPLE 29

In order to prepare 150 g of a 43% atrazine suspension concnetrate, S6.9 g of Stock Solution A (from Example 15) is mixed with 28.6 g of an aqueous solution containing 2.62% of Copolymer 11. To this mixture 64.5 g of atrazine is added, giving a 150 g dispersion, which is homogenized and milled as described in Example 15. The resulting suspension concentrate, to be referred to as Formulation 15, has a composition by weight shown below:

Formulation 15

| Ingredient | Composition, % |
|---|---|
| Atrazine | 43.0 |
| Copolymer 11 | 0.5 |
| Propylene glycol | 4.2 |
| Proxel GXL | 0.44 |
| Rhodorsil 426R | 0.44 |
| Xanthan | 0.06 |
| Water | 51.36 |

Formulation 15 was tested for suspensibility as described in Example 15 and percent suspended atrazine after 4 hours was 93.6±0.3%. A commercial suspension concentrate, Atrazine 4L®, was tested for suspensibility as described in Example 15 and percent suspended atrazine after 4 hours was 56.0±1.4%.

EXAMPLE 30

In order to prepare 150 g of a 43% atrazine suspension concentrate, 56.9 g-of Stock Solution A (from Example 15) is mixed with 28.6 g of an aqueous solution containing 2.62% of Copolymer 9. To this mixture 64.5 g of atrazine is added, giving a 150 g dispersion, which is homogenized and milled as described in Example 15. The resulting suspension concentrate, to be referred to as Formulation 16, has a composition by weight shown below:

Formulation 16

| Ingredient | Composition, % |
|---|---|
| Atrazine | 43.0 |
| Copolymer 9 | 0.5 |
| Propylene glycol | 4.2 |
| Proxel GXL | 0.44 |
| Rhodorsil 426R | 0.44 |
| Xanthan | 0.06 |
| Water | 51.36 |

Formulation 16 was tested for suspensibility as described in Example 15 and percent suspended atrazine after 4 hours was 90.1±0.3%.

EXAMPLE 31

In order to prepare 150 g of a 43% atrazine suspension concentrate, 56.9 g of Stock Solution A (from Example 15) is mixed with 28.6 g of an aqueous solution containing 2.62% of Copolymer 14. To this mixture 64.5 g of atrazine is added, giving a 150 g dispersion, which is homogenized and milled as described in Example 15. The resulting suspension concentrate, to be referred to as Formulation 17, has a composition by weight shown below:

Formulation 17

| Ingredient | Composition, % |
|---|---|
| Atrazine | 43.0 |
| Copolymer 14 | 0.5 |
| Propylene glycol | 4.2 |
| Proxel GXL | 0.44 |
| Rhodorsil 426R | 0.44 |
| Xanthan | 0.06 |
| Water | 51.36 |

Formulation 17 was tested for suspensibility as described in Example 15 and percent suspended atrazine after 4 hours was 94.8±0.3%.

EXAMPLE 32

In order to prepare 150 g of a 43% atrazine suspension concentrate, 56.9 g of Stock Solution A (from Example 15) is mixed with 28.6 g of an aqueous solution containing 2.62% of Copolymer 1A. To this mixture 64.5 g of atrazine is added, giving a 150 g dispersion, which is homogenized and milled as described in Example 15. The resulting suspension concentrate, to be referred to as Formulation 18, has a composition by weight shown below:

Formulation 18

| Ingredient | Composition, % |
|---|---|
| Atrazine | 43.0 |
| Copolymer 1A | 0.5 |
| Propylene glycol | 4.2 |
| Proxel GXL | 0.44 |
| Rhodorsil 426R | 0.44 |
| Xanthan | 0.06 |
| Water | 51.36 |

Formulation 18 was tested for suspensibility as described in Example 15 and percent suspended atrazine after 4 hours was 91.9±0.6%.

EXAMPLE 33

In order to prepare 150 g of a 43% chlorothalonil suspension concentrate, 56.9 g of Stock Solution A (from Example 15) is mixed with 28.6 g of an aqueous solution containing 2.62% of Copolymer 9. To this mixture 64.5 g of chlorothalonil is added, giving a 150 g dispersion, which is homogenized and milled as described in Example 15. The resulting suspension concentrate, to be referred to as Formulation 19, has a composition by weight shown below:

Formulation 19

| Ingredient | Composition, % |
|---|---|
| chlorothalonil | 43.0 |
| Copolymer 9 | 0.5 |
| Propylene glycol | 4.2 |
| Proxel GXL | 0.44 |
| Rhodorsil 426R | 0.44 |
| Xanthan | 0.06 |
| Water | 51.36 |

Formulation 19 was tested for suspensibility as described in Example 15 and percent suspended chlorothalonil after 4 hours was 64.1±0.3%.

EXAMPLE 34

In order to prepare 150 g of a 41% carbaryl suspension concentrate, 56.9 g of Stock Solution A (from Example 15) is mixed with 31.6 g of an aqueous solution containing 2.37% of Copolymer 9 and 12.32% nonionic Agrimer 30® (vinylpyrrolidone homopolymer). To this mixture 61.5 g of carbaryl is added, giving a 150 g dispersion, which is homogenized and milled as described in Example 15. Additional xanthan is added after milling to give a final xanthan concentration of 0.16%. The resulting suspension concentrate, to be referred to as Formulation 20, has a composition by weight shown below:

Formulation 20

| Ingredient | Composition, % |
|---|---|
| Carbaryl | 41.0 |
| Copolymer 9 | 0.5 |
| Agrimer 30 (PVP) | 2.6 |
| Propylene glycol | 4.2 |
| Proxel GXL | 0.44 |
| Rhodorsil 426R | 0.44 |
| Xanthan | 0.16 |
| Water | 50.66 |

Formulation 20 was tested for suspensibility as described in Example 15 and percent suspended carbaryl after 4 hours was 98.8±0.1%. Additional tests were performed as follows: (i) Dispersion and settling tests in Nessler tubes of 1 part Formulation 20 to 50 parts 1000 ppm hard water were completed. Results are shown in Table 2. The suspension concentrate showed good dispersion and negligible settling after 24 hours.

TABLE 2

Initial Bloom, and Appearance and Precipitate Height 24 h after Dilution of Formulation 20 (1/50) in 1000 ppm Hard Water

| Characteristic | Formulation 3 |
|---|---|
| Initial Appearance (Bloom) | Good |
| Appearance after 30 inversions | Excellent |
| Height of foam after 30 inversions (cm) | ½ |
| 1 hour ppt (mm) | None |
| 2 hour ppt (mm) | None |
| 4 hour ppt (mm) | None |
| 24 hrs ppt (mm) | Trace |
| # Inversions needed to redisperse | 2 |

(ii) Accelerated storage of concentrate After 2 weeks storage of 50 ml of Formulation 20 at 52° C. in capped-glass bottles, a liquid phase separation of 3 mm was measured on the top, with no sedimentation detected on the bottom. The suspension concentrate was homogeneous after shaking, and showed no change in viscosity. After 2 weeks storage, the percent suspended carbaryl was 96.8±0.2%. These results indicate Formulation 20 is stable for 2 weeks at 52° C. (iii) Freeze-thaw storage of concentrate Formulation 20 was exposed to freeze-and-thaw temperatures by placing 50 g of the formulation in the freezer at −10° C. for 48 hours followed by placing the formulation in the oven at 30° C. for 48 hours. This freeze-thaw cycle was repeated twice for a total of 3 cycles. Formulation 20 was then tested for suspensibility, yielding a percent suspened carbaryl of 90.3±0.8. (iv) Suspensibility in 5000 ppm hard water Formulation 20 was also tested for suspensibility using 5000 ppm hard water and percent suspended carbaryl after 4 hours was 94.9±0.1%.

EXAMPLE 35

Formulation 21 was prepared identical to Formulation 20 with the exception of replacing Agrimer 30 with Agrimer VA6® (vinylacetate-vinylpyrrolidone copolymer). Formulation 21, has a composition by weight shown below:

Formulation 21

| Ingredient | Composition, % |
| --- | --- |
| Carbaryl | 41.0 |
| Copolymer 9 | 0.5 |
| Agrimer VA6 | 2.6 |
| Propylene glycol | 4.2 |
| Proxel GXL | 0.44 |
| Rhodorsil 426R | 0.44 |
| Xanthan | 0.16 |
| Water | 50.66 |

Formulation 21 was tested for suspensibility as described in Example 15 and percent suspended carbaryl after 4 hours was 98.2±0.2%. Formulation 21 was also tested for suspensibility using 5000 ppm hard water and percent suspended carbaryl after 4 hours was 97.5±0.2%.

EXAMPLE 36

Formulation 22 was prepared identical to Formulation 21 with the exception of replacing Agrimer VA6 with Agrimer AL10® (butylated-vinylpyrrolidone copolymer) Formulation 22, has a composition by weight shown below:

Formulation 22

| Ingredient | Composition, % |
| --- | --- |
| Carbaryl | 41.0 |
| Copolymer 9 | 0.5 |
| Agrimer AL10 | 2.6 |
| Propylene glycol | 4.2 |
| Proxel GXL | 0.44 |
| Rhodorsil 426R | 0.44 |
| Xanthan | 0.16 |
| Water | 50.66 |

Formulation 22 was tested for suspensibility as described in Example 15 and percent suspended carbaryl after 4 hours was 100.2±0.1%. Formulation 22 was also tested for suspensibility using 5000 ppm hard water and percent suspended carbaryl after 4 hours was 98.9±0.1%.

EXAMPLE 37

In order to prepare 150 g of a 41% chlorothalonil suspension, 56.9 g of Stock Solution A is mixed with 31.6 g of an aqueous solution containing 2.37% of Copolymer 9 and 12.32% nonionic Agrimer 30. To this mixture 61.5 g of chorothalonil is added, giving a 150 g dispersion, which is homogenized and milled as described in Example 15. Additional xanthan is added after milling to give a final xanthan concentration of 0.16%. The resulting suspension concentrate, to be referred to as Formulation 23, has a composition by weight shown below:

Formulation 23

| Ingredient | Composition, % |
| --- | --- |
| Chlorothalonil | 41.0 |
| Copolymer 9 | 0.5 |
| Agrimer 30 | 2.6 |
| Propylene glycol | 4.2 |
| Proxel GXL | 0.44 |
| Rhodorsil 426R | 0.44 |
| Xanthan | 0.16 |
| Water | 50.66 |

Formulation 23 was tested for suspensibility as described in Example 15 and percent suspended chlorothalonil after 4 hours was 93.3±0.2%. Additional tests were performed as follows: (i) Dispersion and settling tests in Nessler tubes of 1 part Formulation 23 to 50 parts 1000 ppm hard water were completed. Results are shown in Table 3. The suspension concentrate showed good dispersion and negligible settling after 24 hours.

TABLE 3

Initial Bloom, and Appearance and Precipitate Height 24 h after Dilution of Formulation 23 (1/50) in 1000 ppm Hard Water

| Characteristic | Formulation 6 |
| --- | --- |
| Initial Appearance (Bloom) | Good |
| Appearance after 30 inversions | Excellent |
| Height of foam after 30 inversions (cm) | 1 |
| 1 hour ppt (mm) | None |
| 2 hour ppt (mm) | None |
| 4 hour ppt (mm) | None |
| 24 hrs ppt (mm) | 1 |
| # Inversions needed to redisperse | 7 |

(ii) Accelerated storage of concentrate After 2 weeks storage of 50 ml of Formulation 23 at 52° C. in capped-glass bottles, a liquid phase separation of 3 mm was measured on the top, with no sedimentation detected on the bottom. The suspension concentrate was homogeneous after shaking, and showed and no change in viscosity. After 2 weeks storage, the percent suspended chlorothalonil was 92.1±0.3%. These results indicate Formulation 23 is stable for 2 weeks at 52° C. (iii) Suspensibility in 5000 ppm hard water Formulation 23 was also tested for suspensibility using 5000 ppm hard water and percent suspended chlorothalonil after 4 hours was 88.8±0.3%.

EXAMPLE 38

Formulation 24 was prepared identical to Formulation 23 with the exception of replacing Agrimer 30 with Agrimer VA6. Formulation 24, has a composition by weight shown below:

Formulation 24

| Ingredient | Composition, % |
| --- | --- |
| Chlorothalonil | 41.0 |
| Copolymer 9 | 0.5 |
| Agrimer VA6 | 2.6 |
| Propylene glycol | 4.2 |
| Proxel GXL | 0.44 |
| Rhodorsil 426R | 0.44 |
| Xanthan | 0.16 |
| Water | 50.66 |

Formulation 24 was tested for suspensibility as described in Example 15 and percent suspended chlorothalonil after 4 hours was 92.7±0.3%. Formulation 24 was also tested for suspensibility using 5000 ppm hard water and percent suspended chlorothalonil after 4 hours was 90.3±0.2%.

EXAMPLE 39

Formulation 25 was prepared identical to Formulation 24 with the exception of replacing Agrimer VA6 with Agrimer AL10. Formulation 25, has a composition by weight shown below:

Formulation 25

| Ingredient | Composition, % |
| --- | --- |
| thiophene-substituted carboxamide | 25.0 |
| Copolymer 9 | 0.5 |
| 2-ethylhexylsulfate | 1.0 |
| Agrimer 30 (PVP) | 2.6 |
| Propylene glycol | 4.2 |
| Proxel GXL | 0.44 |
| Rhodorsil 426R | 0.44 |
| Xanthan | 0.16 |
| Water | 65.66 |

Formulation 25 was tested for suspensibility as described in Example 15 and percent suspended chlorothalonil after 4 hours was 93.1±0.3%. Formulation 25 was also tested for suspensibility using 5000 ppm hard water and percent suspended chlorothalonil after 4 hours was 92.4±0.2%.

EXAMPLE 40

In order to prepare 150 g of a 25% a thiophene-substituted carboxamide suspension, 56.9 g of Stock Solution A (from Example 15) is mixed with 31.6 g of an aqueous solution containing 2.37% of Copolymer 9, 12.32% nonionic Agrimer 30, and 4.74% 2-ethylhexylsulfate. To this mixture 37.5 g of a thiophene-substituted carboxamide is added, along with 24 g of water giving a 150 g dispersion, which is homogenized and milled as described in Example 15. Additional xanthan is added after milling to give a final xanthan concentration of 0.16%. The resulting suspension concentrate, to be referred to as Formulation 26, has a composition by weight shown below:

Formulation 26

| Ingredient | Composition, % |
| --- | --- |
| thiophene-substituted carboxamide | 25.0 |
| Copolymer 9 | 0.5 |
| 2-ethylhexylsulfate | 1.0 |
| Agrimer 30 (PVP) | 2.6 |
| Propylene glycol | 4.2 |
| Proxel GXL | 0.44 |
| Rhodorsil 426R | 0.44 |
| Xanthan | 0.16 |
| Water | 65.66 |

Formulation 26 was tested for suspensibility as described in Example 15 and percent suspended thiophene-substituted carboxamide after 4 hours was 93.1±0.3%. Additional tests were performed as follows: (i) Accelerated storage of concentrate After 2 weeks storage of 50 ml of Formulation 26 at 52° C. in capped-glass bottles, a liquid phase separation of 2 mm was measured on the top, with no sedimentation detected on the bottom. The suspension concentrate was homogeneous after shaking, and showed and no change in viscosity. After 2 weeks storage, the percent suspended thiophene-substituted carboxamide was 98.5±0.3%. These results indicate Formulation 26 is stable for 2 weeks at 52° C. (ii) Freeze-thaw storage of concentrate Formulation 26 was exposed to freeze-and-thaw temperatures by placing 50 g of the formulation in the freezer at −10° C. for 48 hours followed by placing the formulation in the oven at 30° C. for 48 hours. This freeze-thaw cycle was repeated twice for a total of 3 cycles. Formulation 26 was then tested for suspensibility, yielding a percent suspened thiophene-substituted carboxamide of 99.6±0.1.

EXAMPLE 41

Granular Formulation

In order to prepare 200 g of a carbaryl granule, 180 g of air-milled carbaryl was mixed with 80 g of an aqueous solution containing 25% Copolymer 11. The dough was extruded through an LCI basket extruder with a 1 mm sreen. The granules were dried in a fluid-bed dryer and the resulting water dispersible granule, to be referred to as Formulation 27, has a composition by weight shown below:

Formulation 27

| Ingredient | Composition, % |
| --- | --- |
| Carbaryl | 86.0 |
| Copolymer 11 | 10.0 |
| Water | 4.0 |

Formulation 27 was tested for suspensibility as described in Example 15 and percent suspended carbaryl after 30 minutes was 79%. In addition, the strength of the granule was measured by first sieving granules between 10 and 40 mesh screens, which isolates granules of lengths between approximately 2.0 and 0.4 mm. 10 g of the sieved granules are placed in a Vanderkamp friabilator containing 25 teflon balls, 6 mm in diameter. The granules are placed in the drum and rotated 400 times. The granules are sieved on a 40 mesh screen and granules remaining on the screen are weighed. Friability index is calculated as [(granule wt remaining on 40 mesh,/10 g)×100]. The friability index for these granules was 91%.

EXAMPLE 42

Seed Coating Formulation

In order to prepare a seed coating formulation, 150 g of a 41% chlorothalonil suspension, 56.9 g of Stock Solution A (from Example 15) is mixed with 31.6 g of an aqueous solution containing 2.37% of Copolymer 9, 12.32% nonionic Agrimer 30, and 4.74% 2-ethylhexylsulfate. To this mixture 61.5 g of chorothalonil is added, giving a 150 g dispersion, which is homogenized and milled as described in Example 15. Additional xanthan is added after milling to give a final xanthan concentration of 0.16%. The resulting suspension concentrate, to be referred to as Formulation 28, has a composition by weight shown below:

Formulation 28

| Ingredient | Composition, % |
|---|---|
| Chlorothalonil | 41.0 |
| Copolymer 9 | 0.5 |
| Agrimer 30 | 2.6 |
| 2-ethylhexylsulfate | 1.0 |
| Propylene glycol | 4.2 |
| Proxel GXL | 0.44 |
| Rhodorsil 426R | 0.44 |
| Xanthan | 0.16 |
| Water | 49.66 |

One part Formulation 28 was mixed with 2 parts of an aqueous solution containing 20% Chromakote Blue dye. 750 grams of soybean seeds (size 2760 seed per lb) were charged into the Hege 11 Liquid Seed Treater. 3 mls of diluted Formulation 26 was applied to the seeds which were then allowed to dry on a glass tray for 30 minutes. Three 250 g portions of the treated seed were each placed on 10 mesh round sieve (8 in. dia., full height. The three sieves were stacked on a CSC Scientific Sieve Shaker, Model #18480, and were shaken for 15 minutes at setting #7. The weight of the dust produced from shaking the treated seeds was 120 mg.

EXAMPLE 43

Wettable Powder Formulation

In order to prepare 200 g of a wettable powder formulation 180 g of carbaryl was mixed with 20 g of Copolymer 5. The mixture was centrifugal-milled using a Glen Mills Mdel ZM1 mill. The powder was then tested for suspensibility according to CIPAC Method #177 and had a percent suspended carbaryl of 57% after 30 minutes.

While the invention has been described with particular reference to certain embodiments thereof, it will be understood that changes and modifications may be made which are within the skill of the art. Accordingly, it is intended to be bound only by the following claims.

What is claimed is:

1. An aqueous, flowable suspension concentrate comprising, by weight: (a) about 20–80% of an agriculturally active chemical, (b) about 0.1–5% of a neutralized alkyl vinyl ether-maleic acid half-ester copolymer as dispersing agent, (c) about 0.05–0.5% of a thickener; and (d) water to 100%, and, optionally, additional wetting agents, which has a pH of about 2–9, which has a storage stability indicative of substantially no settling after 2-weeks at 52° C. and a suspensibility of at least 55% suspended solids after a period of 4-hour settling according to CIPAC Test #MT161.

2. A concentrate according to claim 1 wherein (a) is 30–70%, (b) is 0.2–1.5%, (c) is 0.1–0.2%, and (d) is 30–70%, and the pH is about 3–7.

3. A concentrate according to claim 2 capable of being diluted with water 50–100 times to provide a 1% use formulation which is a sprayable suspension system.

4. A concentrate according to claim 1 wherein (b) also includes vinylpyrrolidone homopolymers and copolymers.

5. A concentrate according to claim 1 further including one or more optional ingredients selected from a biocide, anti-freeze, antifoamer agents, and optionally additional wetting agents.

6. A concentrate according to claim 1 wherein (b) is the ethyl, isopropyl, or butyl half-ester copolymer.

7. A sprayable suspension use formulation comprising the concentrate of claim 1 diluted about 25–1000 times with water.

8. A granular formulation consisting essentially of (a) an agricultural chemical, (b) a neutralized alkyl vinyl ether-maleic acid half-ester copolymer and (c) sufficient water to form the granule.

9. A seed treatment formulation derived from the concentrate of claim 1 which is diluted in the presence of a suitable dye or pigment.

10. A wettable powder formulation consisting essentially of (a) an agricultural chemical and (b) a neutralized alkyl vinyl ether-maleic acid half-ester copolymer.

* * * * *